Aug. 30, 1938. M. H. HORVATH Plant Pat. 287
ROSE
Filed Sept. 1, 1937
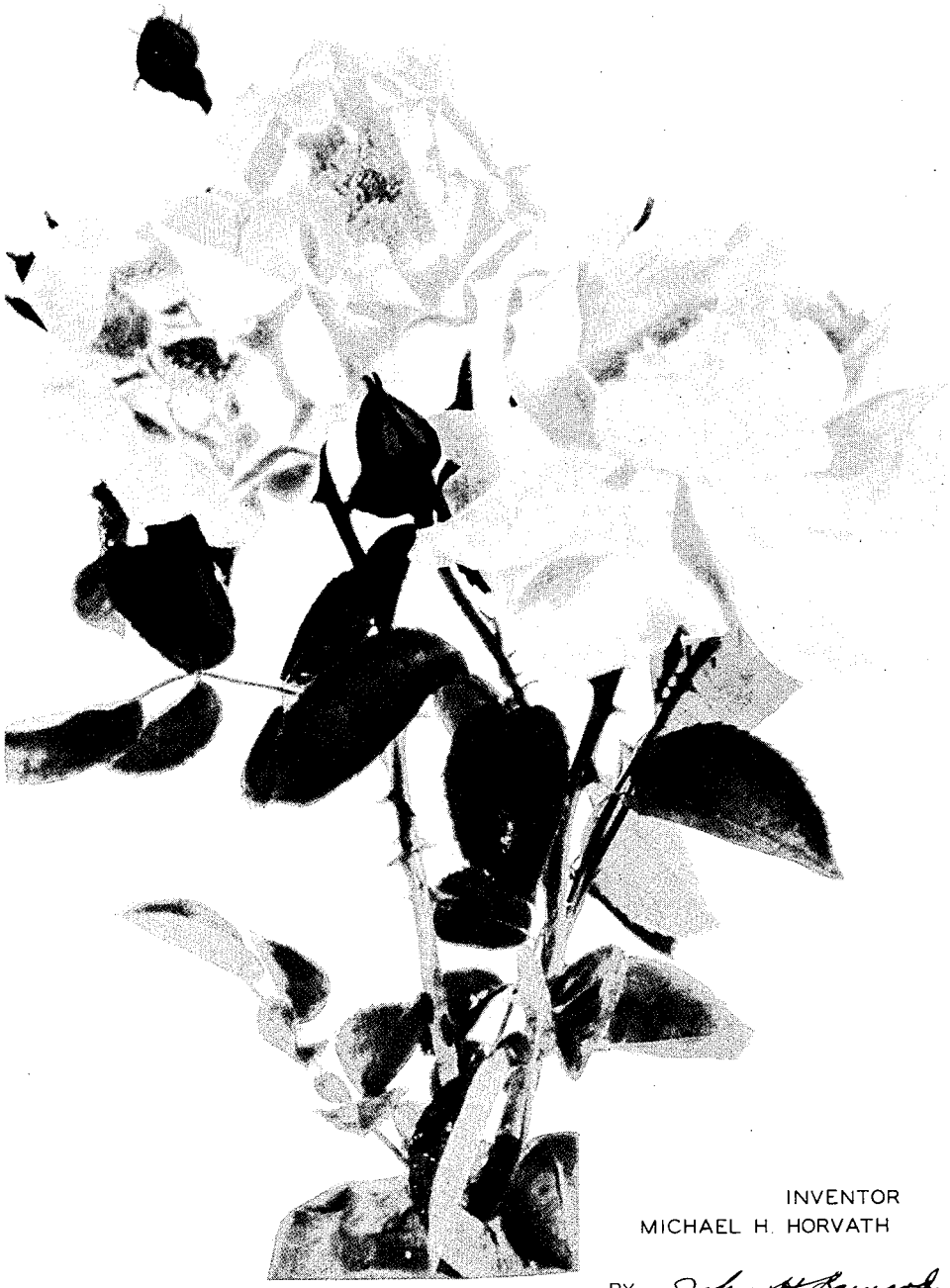
INVENTOR
MICHAEL H. HORVATH
BY John H. Kennard,
HIS ATTORNEY Patented Aug. 30, 1938

Plant Pat. 287

UNITED STATES PATENT OFFICE

287

ROSE

Michael H. Horvath, Mentor, Ohio

Application September 1, 1937, Serial No. 162,061

1 Claim. (Cl. 47—61)

This invention relates to a novel and distinct variety of climbing rose hybridized from "Rosa Setigera" and produced by crossing "Mrs. F. F. Prentiss", as the female parent, with "Director Rubio", as the male parent, and reproduced asexually.

My new rose is distinctly hardy, permitting it to be grown in the temperate region without protection, and with protection in the colder regions where the growing of roses has been exceedingly difficult or impossible.

The shrub has foliage of a very dark rich green color corresponding to Evergreen Plate No. 24E–12 of Maerz and Paul, with a peduncle or main stalk characteristically clean and growing vigorously to a height of some twelve to fourteen feet.

A lively brilliant rose pink, comparable to Plate No. 2H–4, having a lighter center, Plate No. 2I–2, with an iridescent orange undertone, comparable to Plate No. 11L–12, is the flower color. The variety is distinctly floriferous, producing flowers in large quantities in bracts on stems twelve to fourteen inches long and making the flowers excellent for cutting.

The petals, numbering twenty-four to twenty-six for each flower, are wavy and crested, forming charming cup-like, semi-double flowers three to four inches in diameter.

The drawing further illustrates many of the characteristics which are not found in the parent stock and which make the variety of more value as a shrub and enhance its aesthetic value.

Having now fully shown and described my new rose, and the mode of its production, what I claim and desire to secure by Letters Patent of the United States, is:

A rose substantially as herein shown and described and distinguished by the lively brilliant rose pink flowers having a lighter center with an iridescent orange undertone, wavy and crested petals forming cup-like, semi-double flowers, distinctive floriferous character, hardy and vigorous growing plant, rich dark green foliage, and a stem growth excellent for the cutting of flowers.

MICHAEL H. HORVATH.